United States Patent [19]
Langfeld et al.

[11] Patent Number: 5,153,140
[45] Date of Patent: Oct. 6, 1992

[54] PROCESS FOR CONTROLLING AND OPTIMISING INDUSTRIAL PROCESSES FOR THE PREPARATION OF DYES, FLUORESCENT WHITENING AGENTS AND THEIR INTERMEDIATES

[75] Inventors: Horst Langfeld; Roland Minges, both of Grenzach-Wyhlen, Fed. Rep. of Germany; Claudio Puebla, Baton Rouge, La.; Wilhelm Schmidt, Lörrach, Fed. Rep. of Germany

[73] Assignee: Ciba-Geigy Corporation, Ardsley, N.Y.

[21] Appl. No.: 515,025

[22] Filed: Apr. 24, 1990

[30] Foreign Application Priority Data

Apr. 28, 1989 [DE] Fed. Rep. of Germany ....... 3914185

[51] Int. Cl.$^5$ ............................................. G01N 21/33
[52] U.S. Cl. ...................... 436/55; 436/50; 356/351; 250/372; 250/373
[58] Field of Search ............... 436/55, 50; 356/351; 250/373, 372

[56] References Cited

U.S. PATENT DOCUMENTS

| 4,042,328 | 9/1977 | Seymour | 436/100 |
| 4,529,203 | 7/1985 | Girling et al. | 436/3 |
| 4,852,967 | 8/1989 | Cook et al. | 350/96.29 |
| 5,019,515 | 5/1991 | Gisin et al. | 436/52 |

FOREIGN PATENT DOCUMENTS 0273641 7/1988 European Pat. Off. .

OTHER PUBLICATIONS

CAS accession No. 12(4): 30031j.
CAS accession No. 109(4): 29890v.
CAS accession No. 105(12): 107363j.
CAS accession No. 97(26): 223071c.
P. Fitch et al., American Laboratory, Dec. 1985, Model 1000 Chem. Monitors System, Model 200 Optical Waveguide, Model 150 Optical Waveguide, 12 Channel Multiplexer, Sensor & Cable, Unscrambler.
A. Brockes, Journal of the Amer. Assoc. of Textile Chemists & Colorists, 1974, 98/21–103/26.
Jonathan T. Y. Yeh, Chem. Engin. 1986, 55–68.
H. Halvarson, Chemie-Technik, 1986, 91–94.
S. J. Bailey, Control Engin., 1982, 78–80.
H. Schlemmer et al., Fesenius Anal. Chem. 1987, 435–439.
Guided Wave Applic. Note No. A3-987.
J. Blickley, Control Engineering 1986, 83–85.
Jungbauer & Mannhardt brochure.
Messen, Stevern und Regein in der Chemischen, pp. 1–3, 10–17, 52–55, 67–69.
Messen, Stevern und Regein in der Chemischen Technik Band IV, pp. 147–149, 208–210, 215–217.
Lot brochure, "Simultanspektrometer MCS".
Guided wave brochure "Now you can make UV-VIS--NIR analysis in remote locations via fiber optics".
A. van Loosbrock et al., Analytical letters, 1984, 677–688.

Primary Examiner—James C. Housel
Assistant Examiner—David Redding
Attorney, Agent, or Firm—Kevin T. Mansfield; Edward M. Roberts

[57] ABSTRACT

A process for controlling and optimizing chemical industrial processes for the preparation of dyes, fluorescent whitening agents and their intermediates, which process comprises controlling and optimizing those processes by differential analysis of the UV/VIS absorption spectra of at least one starting compound and of at least one reaction product. The advantage of this process is that the actual state of a process can be constantly measured, assessed, and used for feed-back and feed-forward control.

15 Claims, 6 Drawing Sheets

PROCESS FOR CONTROLLING AND OPTIMISING INDUSTRIAL PROCESSES FOR THE PREPARATION OF DYES, FLUORESCENT WHITENING AGENTS AND THEIR INTERMEDIATES

The present invention relates to a novel process for controlling and optimising industrial processes for the preparation of dyes, fluorescent whitening agents and their intermediates by applying the method of UV/VIS absorption spectroscopy to said processes.

In recent years, increasing endeavours have been made to automate and optimise processes for the manufacture of dyes, fluorescent whitening agents and their intermediates, both as regards the manufacturing process itself as well as working up. To obtain satisfactory and reproducible results it is necessary to rely on analytical methods which are characterised by the following criteria: short duration of analysis, high frequency of analysis and greater information content per unit of time, as low costs as possible, simplicity, reliability, ease of automation and minimum space requirements. Equipment that meets these requirements comprises in particular sensors for measuring physical parameters such as pH, temperature, pressure and consumption of starting materials.

These parameters, however, provide no information on the current state and condition of the process (yield of desired product, concentration of by-products, product quality) and the reaction course at any given time. Thus control and maintenance of constant product quality allied to optimum yield is not ensured. Further, it is not possible to make any prognoses from the physical parameters regarding the end point of a reaction, product quality, and yield. Up to now it has been customary to analyse the reaction mass at the end of a process step or of the entire process, thereby ruling out in situ corrections during the reaction course.

Irrespective of the quality of the starting materials, uniform quality of process products together with optimum yield is required at the present time of continuous as well as discontinuous processes for the preparation of dyes, fluorescent whitening agents and their intermediates.

Discontinuous (i.e. batch) processes in particular result easily in fluctuating quality of process products induced by the varying quality of the starting materials, lack of control methods and the yield differs from batch to batch.

Accordingly, it is the objective of the present invention to provide an analytical method that meets the aforementioned requirements and to develop a process for controlling and optimising the processes mentioned above by means of said method, such that control and optimisation can also be carried out on-line.

It has been found that UV/VIS absorption spectroscopy is excellently suited to this purpose.

UV/VIS absorption spectroscopy operates in the wavelength range from ca. 200 to ca. 750 nm. It is a method which has long been known and which, for a great number of chemical compounds, especially those used for the synthesis of dyes, provides a characteristic image as expression of the $\pi$-electron configuration of these compounds.

Compared with other analytical methods such as chromatographic separation methods, UV/VIS absorption spectroscopy affords marked advantages on account of its brief response time, its high frequency, the ease with which it can be automated, its low cost, and its user-friendliness and easy maintenance.

Up to now, the primary field of use for UV/VIS absorption spectroscopy has been the analysis of reaction products for controlling their purity, i.e. the method has been applied at the end of a preparatory process.

Specifically, the present invention relates to a process for controlling and optimising chemical industrial processes for the preparation of dyes, fluorescent whitening agents and their intermediates, which process comprises controlling and optimising said processes by differential analysis of the UV/VIS absorption spectra of at least one starting compound and at least one reaction product.

UV/VIS absorption spectroscopy offers an important feature, as it operates with a directly accessible chemical parameter. As expression of the $\pi$-electron configuration of the investigated substance or reaction mass, the UV/VIS absorption spectrum affords direct access to the quality and purity of the compounds used and obtained, i.e. the actual reaction state and state of a process at the moment of time at which the analysis is made.

The course of the UV/VIS absorption spectra, or the changes in the absorption in the course of a preparatory process, provide direct information which, in the practice of this invention, serves to control and optimise a process.

Suitable technical prerequisites which make the use of UV/VIS absorption spectroscopy in the practice of this invention a rapid, flexible, cost-effective and user-friendly method are typically: computer technology, diode-array spectrophotometer and optical waveguides.

A preferred embodiment of the process of this invention comprises recording UV/VIS absorption spectra of at least one starting compound and at least one reaction product and, in the course of the preparatory process, controlling and optimising the process by differential analysis of the UV/VIS absorption spectrum of the reaction mass and of the UV/VIS absorption spectrum of at least one reaction product, which differential analysis can extend over a wide wavelength.

It has been found generally useful to record and to store in a computer memory UV/VIS absorption spectra of all starting compounds, as a comparison of spectra and substration of spectra enable batch analyses of the individual components to be made with relative ease. In addition, it is possible to carry out analyses of batch ratios when using mixtures of starting compounds as well as a quality control of the starting compounds employed. The condition is that a UV/VIS reference absorption spectrum of preferably each starting compound intended for use in the process is stored so as to control the purity of each new batch and to determine the valid amount of each component.

The UV/VIS absorption spectra of mixtures behave additively, i.e. the UV/VIS absorption spectrum of a mixture of two or more products displays the image of the so-called envelope curve, which corresponds to the sum of the individual spectra in the respective ratio of the mixture components. If suitable envelope curves are stored with the different reactants, then the correct batch ratio of the reactants can be achieved by simple mathametical processing (differential analysis of the actual spectrum with the stored reference spectrum)

and appropriate subsequent charging of one or more components.

The differential analysis of UV/VIS absorption spectra is a qualitative comparison of spectra which can be made purely mathematically and which is independent of concentration, as a comparison of standardised spectra is always made for one extinction and at a selected wavelength. Standardisation is effected, for example, at a wavelength which only shows an absorption for the reaction product.

In batch analysis of reactants, the procedure is typically such that the components are mixed in the desired ratio, and a UV/VIS absorption spectrum is recorded and compared with an appropriate spectrum stored in a computer memory. From the wavelength position of the deviation and the amplitude of the deviation it is possible—if the reference spectrum of each component has been stored in the computer memory beforehand—to determine the missing component or components as well as the respective amount lacking. Upon the conclusion of differential analysis, which shows only a difference within the margin of error, the actual reaction and control and optimisation by means of UV/VIS absorption differential analysis can be commenced.

Industrial processes which may suitably be controlled and optimised by UV/VIS absorption spectroscopy in the practice of this invention are a) processes for the preparation of dyes, fluorescent whitening agents and their intermediates; and b) preferably processes for the preparation of monoazo or polyazo dyes, metal complex azo dyes, anthraquinone, phthalocyanine, formazan, azomethine, nitroaryl, dioxazine, phenazine or stilbene dyes.

Chemical reactions which may suitably be controlled and optimised in the practice of this invention are, in particular, for the processes named in a) and b) above, preferably for dyes, for example diazotisation, coupling, complexing, condensation, oxidation and reduction reactions.

Industrial processes for the preparation of dyes, fluorescent whitening agents and their intermediates result frequently in complex reaction mixtures which are difficult to characterise and which, in their composition, have to be reproduced with the minimum of deviation in order to meet quality requirements. Continual monitoring of the reaction course with the aim of making instant corrections when deviations occur puts stringent demands on the control of the process.

Further, it may be necessary to determine the end point of a reaction rapidly and accurately, as too short a reaction course as well as too long a one may result in differences in the composition of the reaction mixture.

Thus, for example, in the diazotisation of an amine it is not always possible to determine the end point from the control of the nitrite content, as the diazotisation proceeds so slowly at the end of the reaction that scarcely any more nitrite is consumed. If the reaction is discontinued prematurely and the pH is then adjusted for the coupling reaction, the diazotised amine may couple with the non-diazotised amine, resulting in a diminished yield and also failure to achieve the desired shade.

Control and optimisation of the above diazo coupling by UV/VIS absorption spectroscopy makes it possible to verify the actual state by adjusting a sample to a value at which coupling can take place and recording the UV/VIS absorption spectrum and comparing it with a spectrum of a completely diazotised sample. As the coupling takes place upon incomplete diazotisation of the amine, this spectrum shows in part the absorption of an azo compound.

In coupling reactions it may be necessary to avoid an excess of diazo component or of coupling component. In this case too, the end point of the reaction can be accurately determined by means of UV/VIS absorption spectroscopy. Thus, for example, the excess of a coupling component can be determined after taking a sample of the reaction mixture by addition of a diazotised amine.

In some condensation reactions, for example of different aminoazo compounds with a dinitrostilbene, no stoichiometric rules are observed. A poorly definable mixture of azoxy and azo compounds is obtained and also aimed at, the composition of which mixture must be reproduced within relatively narrow limits. The end point of the condensation must be reached exactly, for the desired shade is obtained only if the condensation is complete.

In oxidisation reactions, for example in a copper-catalysed internal cyclisation of a styryl disazo compound, the desired shade is obtained only after complete cyclisation and rapid discontinuation of the reaction. The presence of precursors in the reaction mixture leads to a shift in shade and the end point of the oxidation being overstepped, i.e. the presence of decomposition products results in a dull shade.

In reduction reactions the situation is similar.

The method of UV/VIS spectroscopy can be used for controlling and optimising continuous as well as, in particular, discontinuous preparatory processes.

A particularly preferred embodiment of the process of this invention comprises using the method of UV/VIS absorption spectroscopy for on-line control and optimisation, i.e. the data of the UV/VIS measuring system are standardised in a computer, stored in the computer memory, and in the differential analysis the data are subtracted and compared with any already stored data in order to find the reason for the difference and to take whatever appropriate steps may be necessary to rectify the difference.

A particularly preferred embodiment of the process of this invention comprises controlling and optimising preparatory processes by differential analysis of the concentration ratios of at least one starting compound and of at least one reaction product.

It has been found useful to repeat the differential analysis with specific frequency. This frequency depends on the preparatory process, and a repetition of, for example, 2 to 20 times, preferably of 2 to 5 times, has proved sufficient.

A condition of the differential analysis is that the difference between the spectra from the start of the process to the conclusion of the process of each reaction step becomes smaller.

Suitable parameters for control and optimisation are, for example, temperature, pressure, amount of the starting materials, reaction time and/or pH.

An important embodiment of the process of this invention comprises storing in a computer memory the UV/VIS spectra of at least one starting compound and of at least one reaction product, determining spectroscopically in the course of the preparatory process with specific frequency (e.g. every 30 minutes) the instant state of the reaction by differential analysis of the concentration ratios of the actual state of the reaction mixture and of the desired reaction product, and from this difference, if necessary by changing one or more of the parameters of temperature, pressure, amount of the starting materials, reaction time and/or pH, controlling the difference between the spectra towards zero.

A particularly important embodiment of the process of this invention for controlling and optimising industrial processes for the preparation of dyes, fluorescent whitening agents and their intermediates, comprises storing in a computer memory the UV/VIS absorption spectrum of at least one starting compound and of at least one reaction product in diazotisation, coupling, complexing, condensation, oxidation and reduction reactions, determining spectroscopically in the course of the preparatory process with specific frequency (e.g. every 30 minutes) the instant state of the reaction by differential analysis of the concentration ratios of the actual state of the reaction mixture and of the desired reaction product, and from this difference, if necessary by changing one or more of the parameters of temperature, pressure, amount of the starting materials, reaction time and/or pH value, controlling the difference between the spectra towards zero.

In the practice of this invention, the process control and optimisation usually takes place stepwise, i.e. each process step or stage such as diazotisation, coupling or condensation is controlled and optimised individually. The procedure may be such that, after computing the amount of the components by UV/VIS absorption spectroscopy and after controlling the ratios of the components, the first process step is commenced by first recording a UV/VIS absorption spectrum at the start of the process step and, after standardisation, comparing it with the stored UV/VIS absorption spectrum of the desired reaction product. The differential analysis of the envelope curve of the sum of the reaction components and of the (stored) envelope curve of the reaction result shows the maximum difference. After the start of the reaction, for example by adjusting the temperature or pH value necessary for this process step, further UV/VIS absorption spectra are recorded, standardised, and the above described differential analysis is carried out. The differential analysis should show continually smaller deviations in the course of the process. As position and magnitude of the differential data are known, it is possible to determine for a normal reaction, i.e. one in which each measurement shows a smaller deviation and at the conclusion of the reaction the envelope curves of the reaction mixture and of the stored envelope curve are identical, the optimum time for the completion of the reaction. Further, at specific positions the magnitude of the differential data may increase, thereby indicating, for example, the increased formation of by-products. In such a case, it is the object of the process control and optimisation of this invention to counteract the formation of by-products by changing the process parameters such as temperature, pH and/or addition of starting material. It is, moreover, quite immaterial which measure is taken, as after each measure and recording of a UV/VIS spectrum the differential analysis shows an increasingly smaller difference only if the choice of measure is correct.

It frequently happens in industrial processes that process steps are repeated at specific intervals of time. Hence it is worth while to store in the computer each difference that departs from the normal reaction course and the measure pertaining thereto, so that after several repetitions of the process the correct measure for controlling and optimising the process can be taken immediately by computer control on the basis of the position, magnitude and time of a specific difference.

By means of the process of this invention it is possible to carry out not only those reactions whose UV/VIS absorption spectra differ from one another, for example at the start and at the termination of the reaction, and which yield a soluble product, but also those reactions the control of which can be carried out only by formation of suitable derivatives, for example the conversion of a sulfur or vat dye into the soluble leuco form or, in the case of compounds having very similar UV/VIS absorption spectra, such as reactive dyes containing a fibre-reactive chloro-s-triazine radical and a hydrolysed, no longer fibre-reactive hydroxy-s-triazine radical, the still active component, which gives a UV/VIS absorption spectrum that differs from the hydrolysed component, can be identified by reaction with an amine, for example an arylamine. A further embodiment of the process of this invention thus comprises preparing derivatives of compounds having an unspecific UV/VIS absorption spectrum or a difference insufficient for analysis, and carrying out the control and optimisation using the derivatives of said compounds. The derivatisation can be effected, for example, by means of the FIA (flow injection analysis) technique.

For the process of this invention it is necessary to take the sample for spectrophotometric analysis with specific frequency from the reaction medium; or the measurement is made direct in the reaction medium, for example using an optical sensor by the ATR (attenuated total reflection) technique. The advantage of this technique is, for example, that no working up of the sample is necessary.

It is also convenient to link the measuring site and the appropriate measuring system with each other by means of optical waveguides, so making possible a signal transmission over wide areas of, for example, up to 1000 m, which transmission is not hindered by electrical or magnetic fields. A further advantage of optical waveguides is that no special measures need be taken regarding explosion prevention.

Surprisingly, the process of this invention not only makes it possible to determine and monitor the instant state of the process, e.g. the yield of final product so far obtained and the concentration of by-products, but also, on account of the substantial amount of relevant data per unit of time resulting from the method of UV/VIS absorption spectroscopy and differential analysis, to drive the process to a desired quality (composition of process products) by using the data obtained in the detector for process control (feed-back or, preferably, feed-forward control). Further, each new analysis affords a prognosis on the further reaction course and on the end point of the reaction.

The following information to be used for process control is obtained by measuring e.g. spectral data during the reaction:

the optimum time for terminating the reaction,
control of yield,
control of reaction conditions in that deviations from normal are expressed by e.g. increased formation of by-products,
quality control by determining and identifying by-products.

The dyes whose synthesis and processing are monitored and controlled by the method described herein are dyes for substrates of any kind, especially paper, leather and textile dyes. Primarily they are textile dyes belonging to the widest possible range of chemical classes. These are e.g. anionic dyes such as nitro, aminoketone, ketoneimine, methine, nitrodiphenylamine, quinoline, aminonaphthoquinone or coumarin dyes or also acid dyes based on fustic extract, in particular acidanthraquinone and azo dyes such as monoazo, disazo and polyazo dyes. Also suitable are basic, i.e. cationic, dyes. These dyes are typically the halides, sulfates, methosulfates or metal halide salts, for example tetrachlorozincates, of azo dyes such as monoazo, disazo and polyazo dyes, of anthraquinone dyes and phthalocyanine dyes; diphenylmethane and triarylmethane dyes; methine, polymethine and azomethine dyes; of thiazole, ketoneimine, acridine, cyanine, nitro, quinoline, benzimidazole, xanthene, azine, oxazine and thiazine dyes. Preferred dyes are those mentioned above.

In the present context, the term "dyes" shall also be understood as meaning fluorescent whitening agents, for example, stilbene whiteners, in particular those of the bistriazinylaminostilbenedisulfonic acid type, of the bis(styrylbiphenyls) and of the bis(triazolylstilbene)disulfonic acids.

It will be readily appreciated that, depending on the situation arising from the dye synthesis, precursors and by-products are also encompassed by the process of this invention in addition to dyes and fluorescent whitening agents. The by-products formed during the reaction are especially of great importance, not only with regard to yield, but also as regards shade or the intrinsic colour of the respective dye and/or fluorescent whitening agent.

In principle, the process is susceptible of very broad application and can be used in dye manufacture for monitoring and controlling dye synthesis, for monitoring and controlling educt and product streams, for analysis and for quality control.

The technique of UV/VIS absorption spectroscopy with differential analysis affords the possibility of near real-time monitoring or direct control of a process. A particularly suitable measuring system has been found to be a diode-array spectrophotometer.

In the manufacture of dyes and their intermediates, it is an object, in addition to obtaining as high a yield as possible, to prepare a specific type or to run the process in such a manner that reproducibly standardised products are obtained.

For adjusting dyes of a specific type, the classical procedure is to exhaust the sample to be adjusted—blended with different amounts of shading dye—and the dye type in one batch on to the substrate, preferably the textile material. In difficult cases, several shading dyes are also tried out, or initially a rough colour gradation is effected, followed by a finer gradation. Assessment is made visually, checking not only for colour matching, but also with less reliable interpolations having to be made. The procedure is highly labour-intensive and requires a high level of technical skill.

For this reason a changeover has been made to assessing the dyeing by remission measurements. This requires the kind of level dyeing obtained, for example, in piece dyeing. Yarns have poor suitability.

A substantial rationalisation of adjustment, however, is only possible if the complicated and error-prone dyeing can be eliminated. The requirement here is that the liquors can be described colorimetrically and that a correlation exists between the colour point of the liquor and the colour point of the dyeing.

The adjustment of the sample is made such that suitable solutions of the type to be prepared, of the sample and of the shading dyes or of the samples to be mixed are measured photometrically. In a second step, colour points are computed from these values. Colour differences can then be ascertained from these colour points and from these colour differences, finally, mixture ratios, such that the remaining colour differences between the type to be prepared and the mixture are as small as possible.

Several colour spaces are known for the colour coordinates to be computed.

Common to all methods of computation is the fact that they yield reliable results only for small colour differences, that they relate only to one standard source of light, and that they permit metameric dyeings. Metameric dyeings are those which have different spectra, but—with respect to a standard source of light—have identical colour points. Their behaviour differs with respect to other sources of light and—which is especially troublesome—information on the relationship between colour point of the liquor/colour point of the dyeing is unreliable.

Colour points are not well suited to production control: a shift in shade to green can be interpreted not only as an excess of a green component, but also as an excess of a blue component and also an excess of a red component or as an excess of only blue (only yellow).

The process of this invention for controlling and optimising processes for the preparation of dyes by means of UV/VIS absorption spectroscopy and differential analysis makes it possible not only to control and optimise the actual process, i.e. the chemical reaction, but also the standardised adjustment of the product. Position and extent of the deviation are known from the data of the differential analysis. When monitoring reactions in which, for example, there is increased formation of by-products, a standardised reaction product can be obtained immediately after the synthesis with the aid of suitable shading dyes.

A special advantage of UV/VIS absorption spectroscopy is the high measuring frequency, which makes feed-forward control possible.

Another preferred embodiment of the process of this invention comprises applying to the control and optimisation of processes for the preparation of dyes, fluorescent whitening agents and their intermediates, the method of UV/VIS absorption spectroscopy, especially of differential analysis of UV/VIS absorption spectra, wherein the analyzer (process analyzer) consists of
 a sample taking system and, optionally, a sample processing system,
 a measuring cell,
 an optical waveguide system, and
 a detector
said sample taking system consisting preferably either of a valve for completely dissolved samples, or of a valve connected to a unit for continuous filtration, homogenisation and/or dilution of sample with a solvent or a membrane, whereby only portions of the sample relevant for the analysis, or only dissolved amounts of the sample, are fed into the analyzer system.

A suitable measuring cell is, for example, a commercially available UV cuvette; or the transmission is effected direct in the reaction medium, for example by means of an optical sensor.

A suitable optical waveguide system comprises, for example, an arrangement of parallel optical waveguides. The measuring beam is directed via one waveguide and the exiting beam is diverted via the other.

A suitable detector is, in particular, a diode array spectrophotometer.

Preferred procedures comprise using the method of UV/VIS absorption spectroscopy for controlling and optimising acylation reactions (acylation will be understood as meaning in particular the condensation of a fibre-reactive or fibre-nonreactive acyl radical with an amine, a hydroxyl group or a thiol group), diazotisations, coupling reactions metallisation reactions, or condensation reactions.

The process of the invention is used, for example for determining the concentration of starting materials and/or products in the above mentioned processes;

for analysing the starting material/product concentration ratio and for determining the concentration of by-products in the synthesis of dyes, fluorescent whitening agents and their intermediates;

for on-line control of a computer-integrated, automated preparatory process;

for on-line control of a computer-integrated, automated process for the preparation of dyes, fluorescent whitening agents and their intermediates;

for shading a pre-selected hue in the manufacture of dyes.

The invention is illustrated by the following Examples in which parts and percentages are by weight. The relationship between parts by weight and parts by volume is the same as that between the gram and cubic centimeter.

EXAMPLE 1

Preparation of the dye of formula

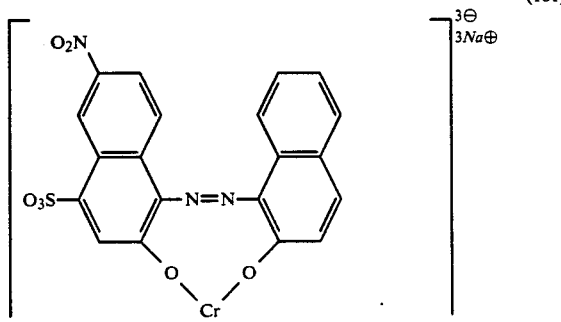
(101)

-continued

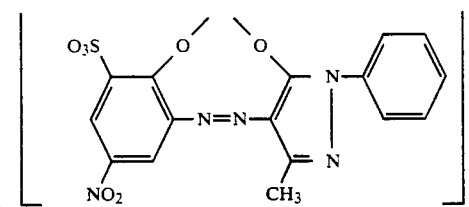

A UV/VIS absorption spectrum is recorded of a pure standardised sample of the dye of formula (101) and the data are stored in a computer.

A UV/VIS absorption spectrum is recorded of ca. 180 parts of the coupling mixture of the monoazo dye of formula

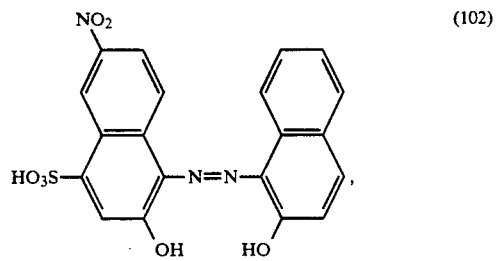
(102)

(prepared from 60.7 parts of 1-diazo-2-hydroxy-6-nitronaphthalene-4-sulfonic acid by coupling to 30.9 parts of 2 naphthol), and the data are stored in a computer. With good stirring, 80 parts of the dye of formula

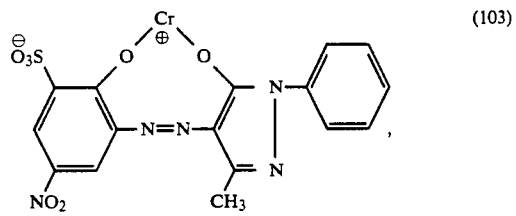
(103)

whose absorption data are also stored in a computer, are added at pH 6 and 80° C. to the coupling mixture. The pH falls meanwhile to 3-3.5. The pH is adjusted once more to 6 with 50% NaOH solution, and the batch is stirred until the pH remains constant.

During the reaction, a UV/VIS absorption spectrum of the reaction mixture is recorded and compared with the reference spectrum of the dye of formula (101). Three of the possible deviations are illustrated below.

Figure 1A:
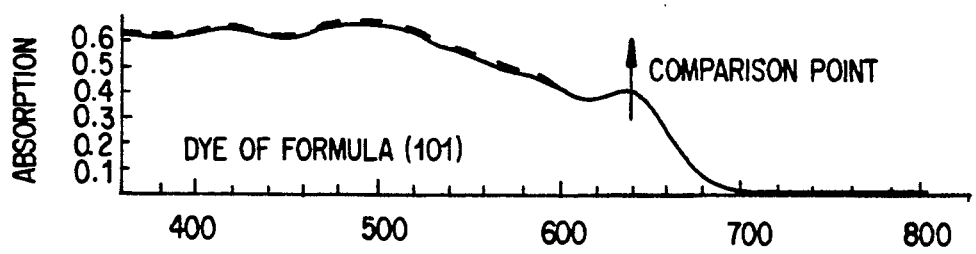
FIGS. 1 to 3 are schematics of the reference spectrum of a compound, deviating instant spectra of the reaction mixture, as well as sources for correcting the mixture balance in order to rectify the deviation.
Figure 1B:
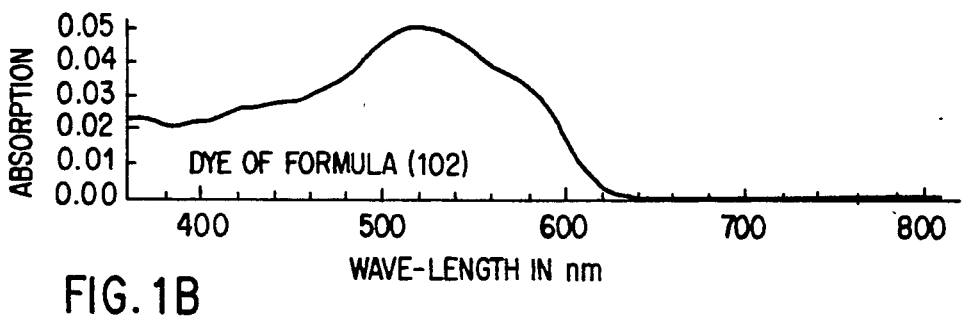

FIG. 1 shows in the top part a solid line which corresponds to the reference spectrum of the dye of formula (101), and a broken line which represents the deviation of the spectrum of the reaction mixture from the reference spectrum. Both spectra are standardised at the indicated comparison point of 618 nm. The deviation in the range from 450 to 575 nm lies exactly in the wavelength range in which the dye of formula (102) absorbs strongly. In the lower part of the figure, the spectrum of the dye of formula (102) is shown.

As measure for controlling the preparatory process, the dye of formula (103) is added in small increments (twice 2 parts) until no further deviation is detectable.

Figure 2A:
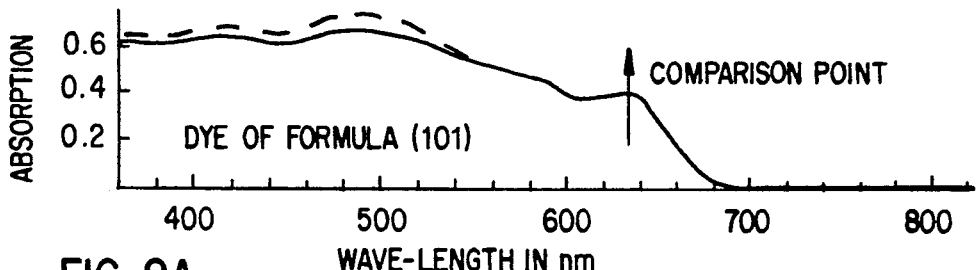
Figure 2B:
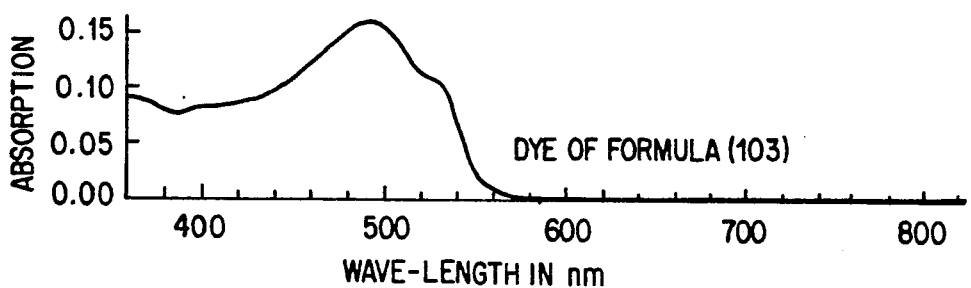

FIG. 2 shows in the top part a solid line which corresponds to the reference spectrum of the dye of formula (101), and a broken line which represents the deviation of the spectrum of the reaction mixture from the reference spectrum. Both spectra are standardised at the indicated comparison point of 618 nm. The deviation in the range from 450 to 520 nm lies exactly in the wavelength range in which the dye of formula (103) absorbs strongly. In the lower part of the figure, the spectrum of the dye of formula (103) is shown.

As measure for controlling the preparatory process, the dye of formula (102) is added in small increments (twice 2 parts) until no further deviation is detectable.

Figure 3A:
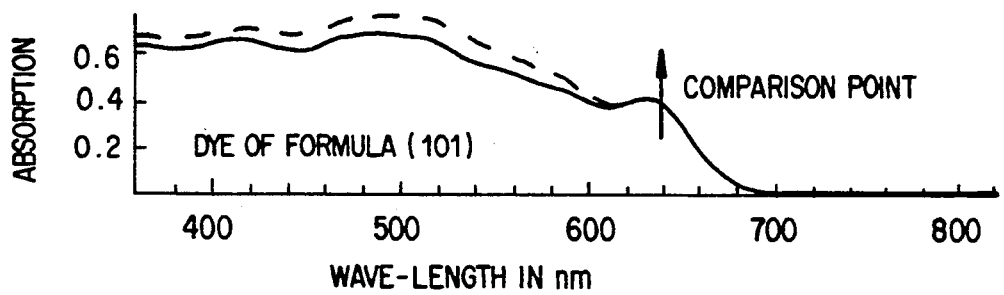
Figure 3B:
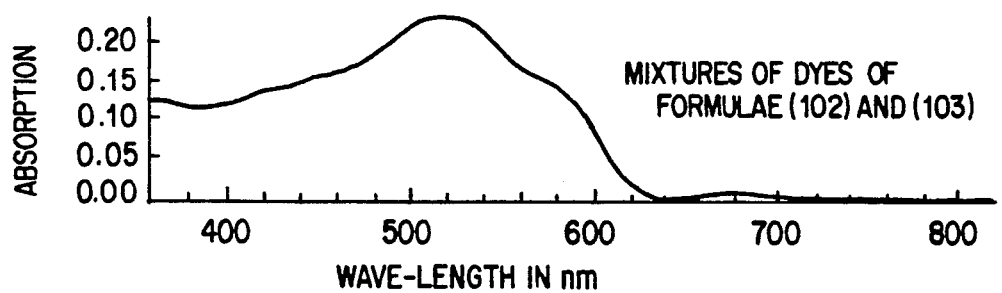

FIG. 3 shows in the top part a solid line which corresponds to the reference spectrum of the dye of formula (101), and a broken line which represents the deviation of the spectrum of the reaction mixture from the reference spectrum. Both spectra are standarised at the indicated comparison point of 618 nm. The deviation in the range from 450 to 575 nm lies exactly in the wavelength range in which the mixture of the dyes of formulae (102) and (103) absorbs strongly. In the lower part of the figure, the spectrum of the mixture of the dyes of formulae (102) and (103) is shown.

The deviation in the wavelength range from 400 to 575 nm documents a relatively high proportion of unreacted starting materials.

As measure for controlling the preparatory process, it must first be verified whether the temperature of 80° C. is being maintained. If the temperature has fallen, the temperature adjustment is corrected and the further reaction course is monitored spectroscopically until no further deviation is detectable. If, however, the temperature adjustment is error-free, then the pH is controlled. If the pH shows a deviation, it is adjusted to 6 and the further reaction course is monitored spectroscopically until no further deviation is detectable. If, however, the adjustment of the pH is error-free, the reaction time is prolonged and the reaction is monitored spectroscopically until no further deviation from the reference spectrum is detectable.

If the spectrum of the reaction mixture exhibits no deviation from the reference spectrum, then the reaction is complete and is discontinued.

A further possible deviation of the reaction not illustrated here is the formation of symmetrical 1:2 chromium complex compounds.

EXAMPLE 2

Preparation of a dye which in the form of the free acid has the formula

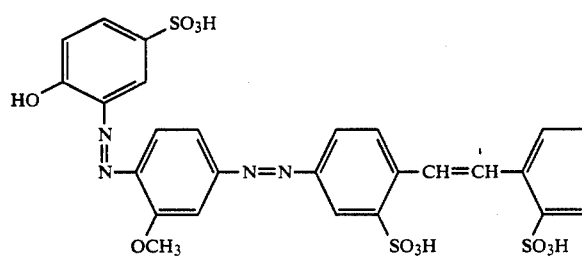

in accordance with the particulars of the Example in the Table, line 50, on page 5 of DE-C 746–455. The condensation of the components after addition of the base is subsequently described, for example in Example 5 of the above patent specification, where the condensation is complete after 18 hours.

Figure 4A:
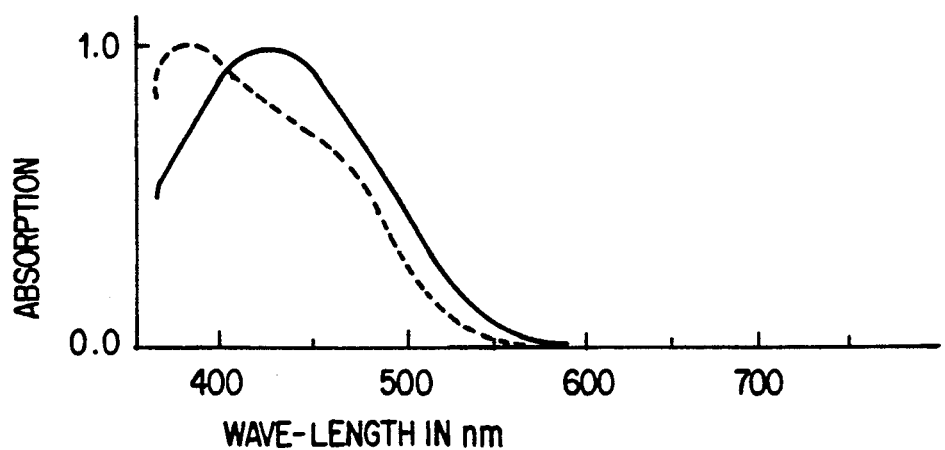
FIGS. 4a to 8b are schematics of the course of a condensation reaction indicating the reference spectrum of a compound, deviating instant spectra of the reaction mixture after 60, 120, 180 and 210 minutes, as well as the difference between the respective spectra.
Figure 4B:
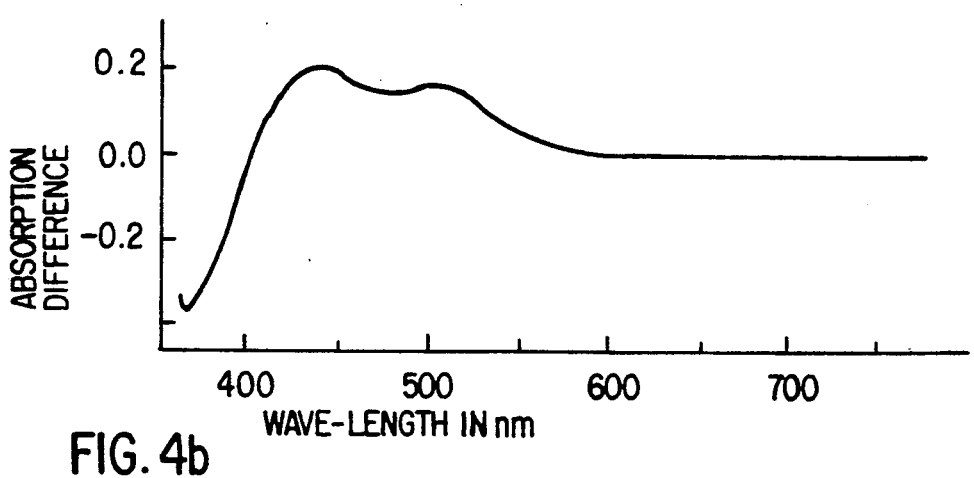

The solid line in FIG. 4a is the reference spectrum of the dye of formula (104) after the condensation, and the dotted line is the spectrum of the mixture of the components before the condensation. FIG. 4b shows the difference between both spectra in FIG. 4a.

Figure 5A:
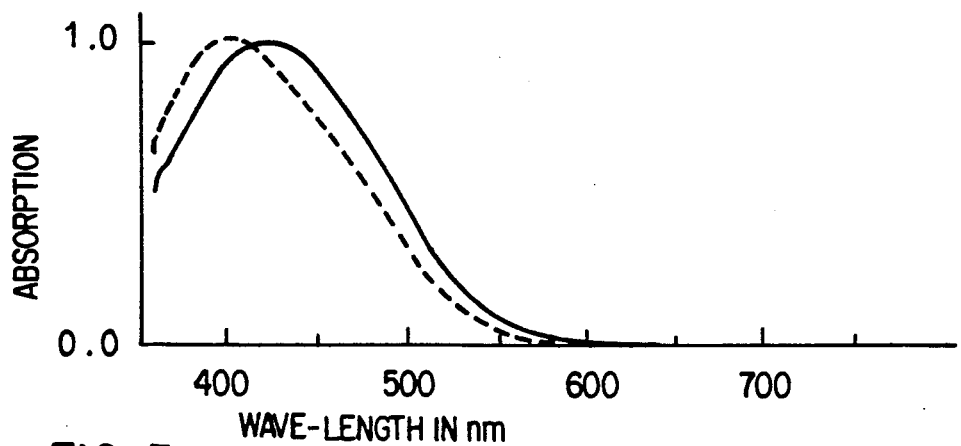
Figure 5B:
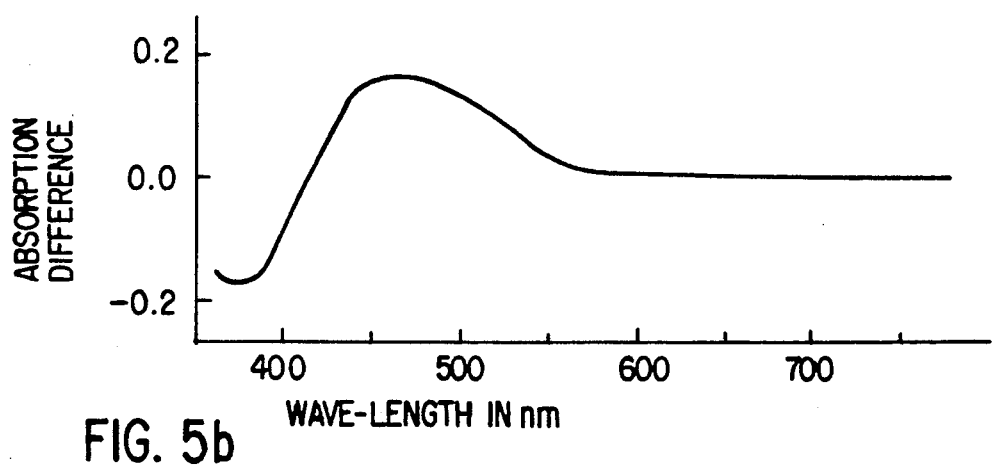

The solid line in FIG. 5a is the reference spectrum of the dye of formula (104) after the condensation, and the dotted line is the spectrum of the reaction after condensation for 60 minutes at 100° C. FIG. 5b shows the difference between both spectra in FIG. 5a.

Figure 6A:
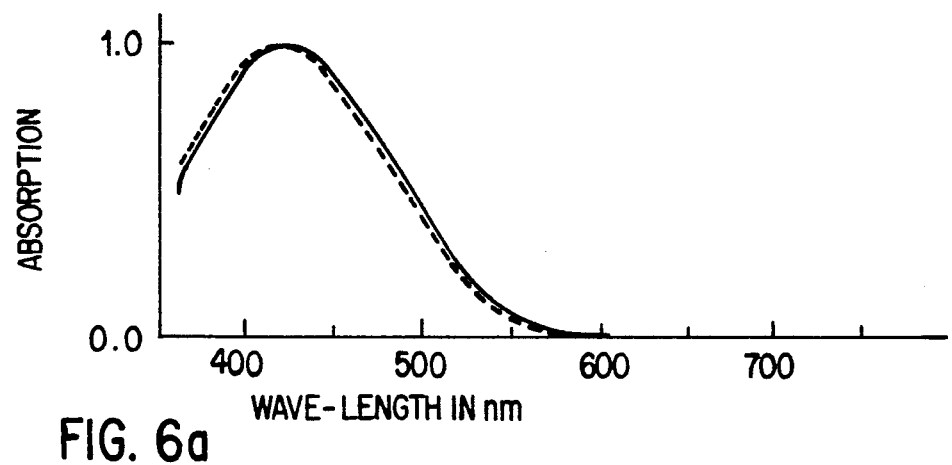
Figure 6B:
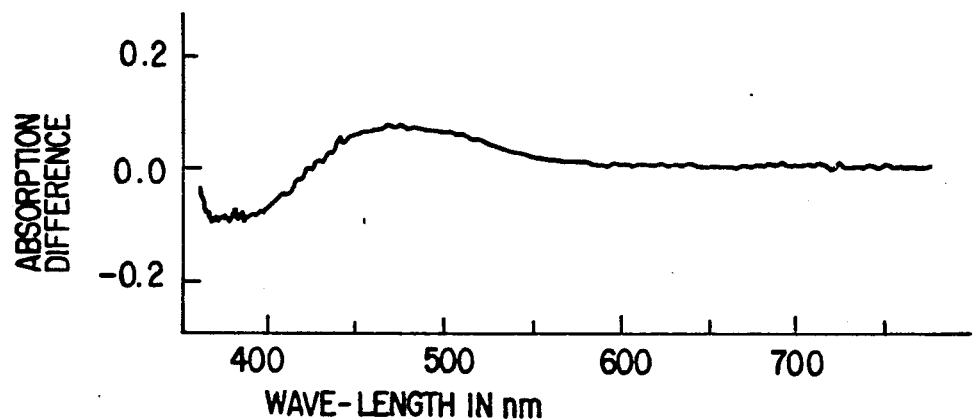

The solid line in FIG. 6a is the reference spectrum of the dye of formula (104) after the condensation, and the dotted line is the spectrum of the reaction after condensation for 120 minutes at 100° C. FIG. 6b shows the difference between both spectra in FIG. 6a.

Figure 7A:
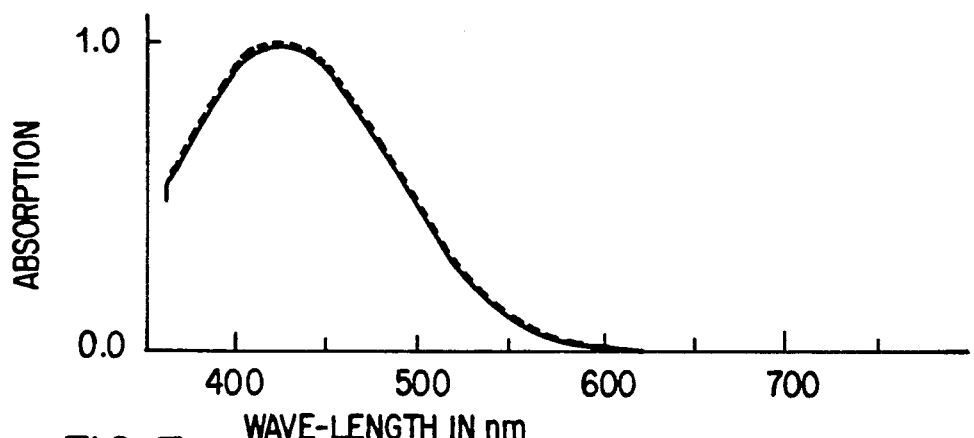
Figure 7B:
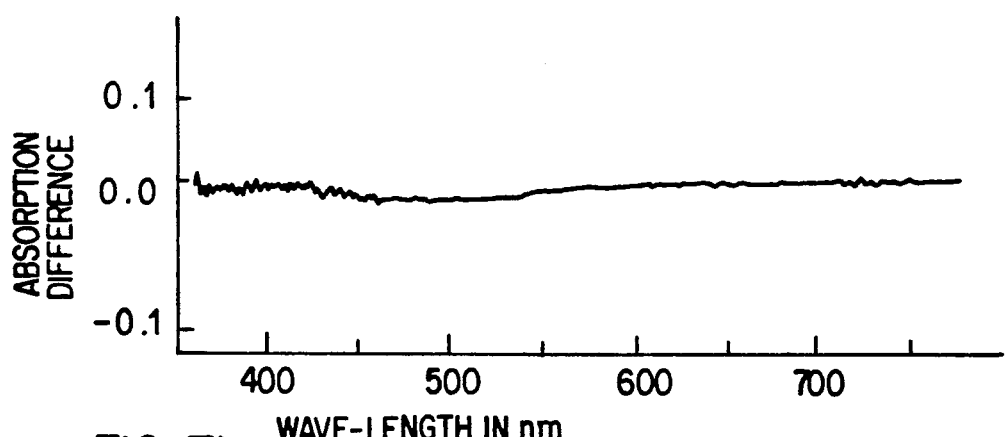

The solid line in FIG. 7a is the reference spectrum of the dye of formula (104) after the condensation, and the dotted line is the spectrum of the reaction after condensation for 180 minutes at 100° C. FIG. 7b shows the difference between both spectra in FIG. 7a.

Figure 8A:
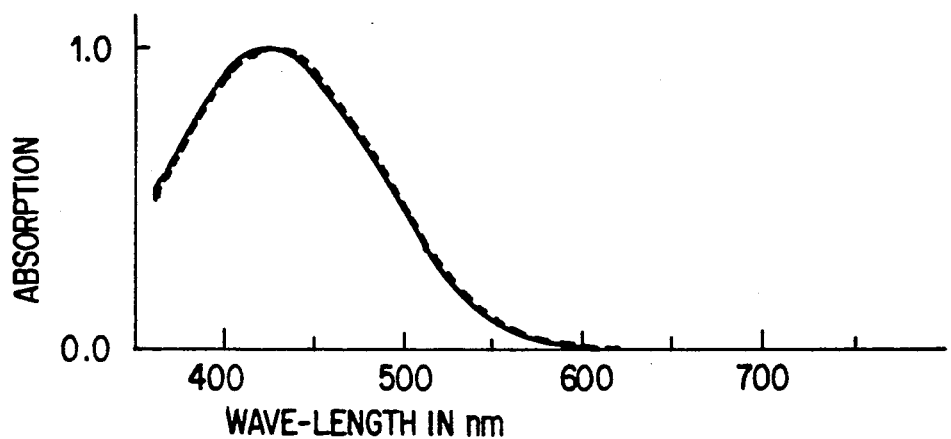
Figure 8B:
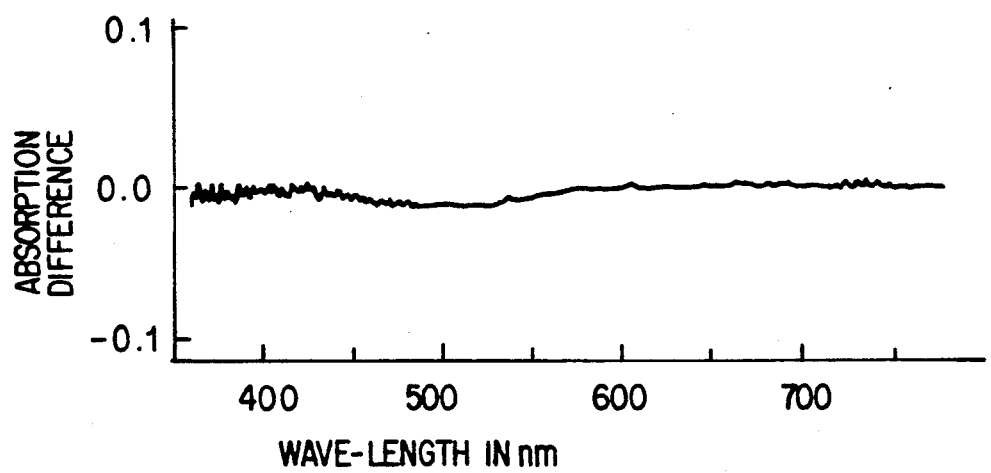

The solid line in FIG. 8a is the reference spectrum of the dye of formula (104) after the condensation, and the dotted line is the spectrum of the reaction after condensation for 210 minutes at 100° C. FIG. 8b shows the difference between both spectra in FIG. 8a.

The difference between the spectra 4a, 5a, 6a and 7a, shown in FIGS. 4b, 5b, 6b and 7b, exhibit an ever diminishing amount of difference. The difference between the spectra 7a and 8a, shown in FIGS. 7b and 8b, is almost identical, i.e. the condensation is complete and is discontinued. The dye of formula (104) can be subsequently coppered.

In contradistinction to the particulars of DE-C 746 455, wherein the condensation is interrupted only after 18 hours, the reaction controlled by UV/VIS absorption spectroscopy and differential analysis is terminated after 3½ hours.

In accordance with the particulars of DE-C 746 455, by changing the ratios of aminoazo compounds to the dinitrostilbenedisulfonic acid and by modifying the condensation conditions, for example changing the condensation volume, alkalinity or condensation temperature, it is possible to obtain a reaction product which, after coppering, dyes cotton in olive-green to greenish-grey shades. To obtain a reproducible reaction result, the current state of the condensation must be monitored and controlled, for example, by changing the tempera-

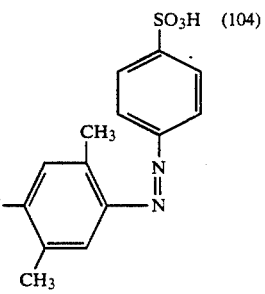

ture or pH.

EXAMPLE 3

1-Aminonaphthalene-5-sulfonic acid is diazotised with sodium nitrite in conventional manner at pH 1 and a temperature of 0°-5° C. The nitrite consumption is initially very rapid, and at the conclusion of the diazotisation very slow. The end point of the diazotisation is difficult to determine from the control of excess nitrite and the result is a premature discontinuation of the reaction. The supposedly completely diazotised compound is adjusted, prior to coupling to a coupling component, to a pH of ca. 3.5, whereupon non-diazotised 1-aminonaphthalene-5-sulfonic acid and the diazotised component react to give the red dye of formula (105)

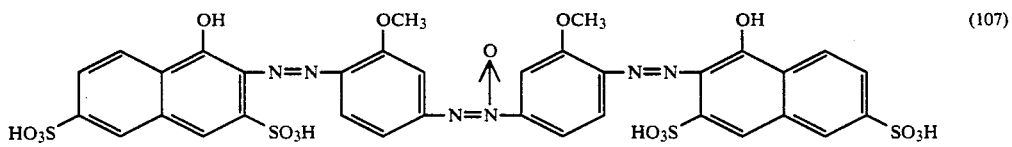

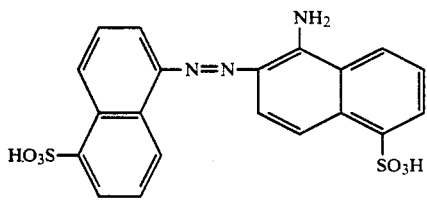

Sufficient diazotised amine is no longer available for the subsequent coupling, so that the reaction is incomplete and the desired shade is spoiled by the dye of formula (105).

To control this diazotisation by UV/VIS absorption spectroscopy, the UV/VIS absorption spectrum of a completely diazotised sample is recorded and stored as reference spectrum. In the course of the diazotisation, samples are taken from the reaction mixture at an interval of 30 minutes, adjusted to pH 4.0 with sodium acetate, and the absorption spectrum is recorded each time such that the incomplete diazotisation is shown by the formation of the dye of formula (105) and a corresponding absorption at ca. 500 nm. When the spectrum of the reaction mixture shows no deviation from the reference spectrum, the diazotisation is complete and the reaction is discontinued.

EXAMPLE 4

The dye of formula (106)

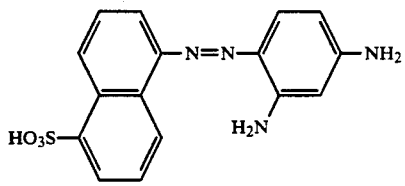

is obtained by addition of diazotised 1-aminonaphthalene-5-sulfonic acid according to Example 3 to an aqueous solution of 1,3-phenylenediamine at pH 7.5-8.0 and 15°-20° C. over 30 minutes. The pH falls during this addition to 4.0-4.5. The reaction is very rapid. The feed contains 95% of the intended coupling component. The remaining 5% is added stepwise while constantly checking for an excess of coupling component. In addition, a sample of the reaction mixture is diluted each time and treated with a small amount of an aqueous buffered solution of diazotised 4-nitroaniline, and the absorption spectrum is recorded. Excess 1,3-phenylenediamine and diazotised 4-nitroaniline give a strong orange dye, so displacing the reference spectrum hypsochromically.

EXAMPLE 5

The preparation of the dye intermediate of formula is effected by reductive condensation of the monoazo compound of formula

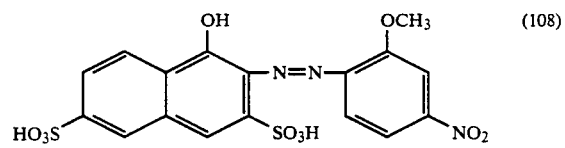

in aqueous medium at 53° to 55° C. and at a pH of at least 12, in the presence of glucose. The resultant reaction mixture contains the compound of formula (107) as main component. The reaction is not selective. Under the reaction conditions, the reductive condensation does not remain in the stage of the compound of formula (107), but the reaction mixture decomposes on prolongation of the reaction time. The end point of the reduction condensation must be determined accurately and the reaction discontinued immediately.

To control the process by means of UV/VIS absorption spectroscopy, it is necessary to store a spectrum of the monoazo compound of formula (108) as well as a spectrum of the desired final product in the computer, and to monitor the reaction course spectroscopically. The absorption maximum of the monoazo compound of formula (108) is in the region of ca. 500 to 540 nm, and the absorption maximum of the desired final product is in the region of ca. 570 to 610 nm. As soon as the difference between the absorption spectrum of the reaction mixture and of the stored spectrum is within the margin of error, the addition of reducing agent is discontinued.

After demethylating coppering of the compound of formula (107), a dye is obtained which dyes paper in blue shades.

EXAMPLE 6

The dye of formula

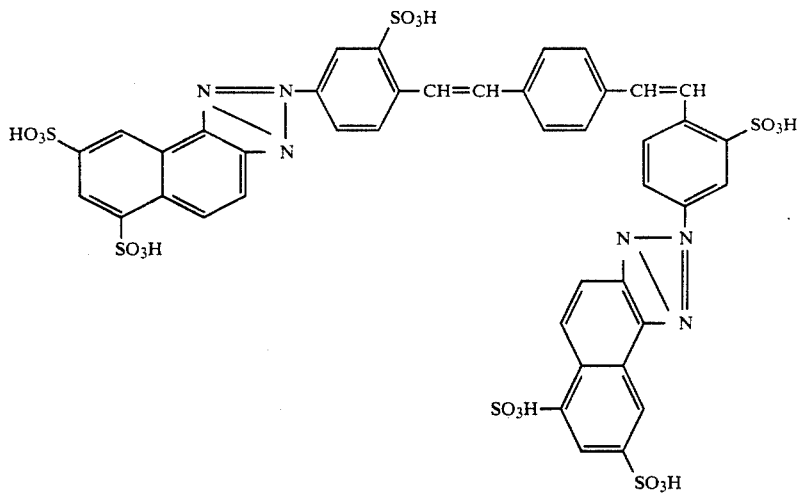

(109)

is prepared by a copper-catalysed internal cyclisation of the compound of formula

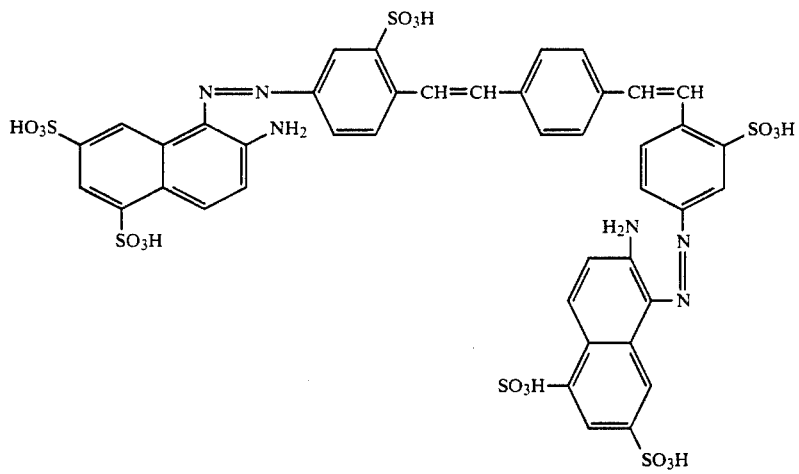

(110)

The oxidising condensation is carried out in aqueous medium at a temperature in the range from 95° to 97° C. and at a pH from 12.5–12.8, in the presence of CuSO$_4$ over the course of 8 to 10 hours. The desired dye, which dyes cotton in a brilliant yellow shade, is obtained only after complete cyclisation and immediate discontinuance of the reaction by acidifying the reaction mixture. The presence of unreacted dye of formula (110) results in a shift of the colour to red. As a consequence of the end point of the reaction being exceeded, the reaction mixture contains decomposition products and gives a dull yellow shade on cotton.

To control the process by UV/VIS absorption spectroscopy, it is necessary to store a spectrum of the compound of formula (110) as well as a spectrum of the desired final product and to monitor the reaction course spectroscopically. The absorption maximum of the compound of formula (110) is in the region of ca. 500 to 520 nm and the absorption maximum of the desired final product is in the region of ca. 400 nm. As soon as the difference between the absorption maximum of the reaction mixture and of the stored spetcrum lies within the margin of error, the reaction is discontinued by acidification.

What is claimed is:

1. A process for on-line controlling and optimising industrial chemical metallising and condensation reactions for the preparation of dyes using the method of UV/VIS spectroscopy, which process comprises recording the UV/VIS absorption spectra of at least one starting compound and of at least one reaction product, determining spectroscopically in the course of the preparatory process at specific time intervals the present state of the reaction by differential analysis of the instant UV/VIS absorption spectrum of the reaction mass and of the UV/VIS absorption spectrum of at least one reaction product, and from this difference, if necessary by changing one or more of the parameters of temperature, pressure, amount of the starting materials, reaction time or pH value, controlling the difference between said last two spectra towards zero.

2. A process according to claim 1, which comprises controlling and optimising processes for the preparation of monoazo or polyazo dyes, metal complex azo dyes, anthraquinone, phthalocyanine, formazan, azomethine, nitroaryl, dioxazine, phenazine or stilbene dyes.

3. A process according to claim 1, which comprises using the method of UV/VIS spectroscopy for controlling and optimising discontinuous preparatory processes.

4. A process according to claim 1, which comprises controlling and optimising preparatory processes by differential analysis of the concentration ratios of at least one starting compound and of at least one reaction product.

5. A process according to claim 1, which comprises storing in a computer the UV/VIS absorption spectrum of at least one starting compound and of at least one reaction product in a metallising or condensation reaction, determining spectroscopically in the course of the preparatory process at specific time intervals the present state of the reaction by differential analysis of the concentration ratios of the instant state of the reaction mixture and of the desired reaction product, and from this difference changing one or more of the parameters of temperature, pressure, amount of the starting materials, reaction time or pH value, controlling the difference between said spectra towards zero.

6. A process according to claim 1, which comprises preparing the derivative of a compound having an unspecific UV/VIS spectrum or a difference insufficient for analysis, and carrying out control and optimisation using said derivative.

7. A process according to claim 1, which comprises taking the sample for spectrophotometric analysis either from the reaction medium and, in a subsequent optional step, working up said sample, or carrying out the measurement in the reaction medium with the aid of an optical sensor.

8. A process according to claim 1, wherein the sample for analysis and the UV/VIS measuring system are linked to each other by optical waveguides.

9. A process according to claim 1, which comprises the use of a diode-array spectrophotometer as UV/VIS measuring system.

10. A process as claimed in claim 1, which comprises determining the concentration of starting materials or of product/by-product ratios in a preparatory process according to claim 2.

11. A process as claimed in claim 1, which comprises analysing the starting material/product ratio and determining the concentration of by-products in a preparatory process according to claim 2.

12. A process as claimed in claim 1, which comprises the on-line control of a computer-integrated, automated preparatory process.

13. A process as claimed in claim 1, which comprises shading a preselected hue in the synthesis of dyes.

14. A process according to claim 1, which comprises controlling and optimising metallisation reactions and the condensation reactions of different aminoazo compounds with dinitrostilbene.

15. A process according to claim 7, wherein the sample for analysis is taken from the reaction medium by by-pass or value.

* * * * *